United States Patent [19]

Beach et al.

[11] 4,293,502

[45] Oct. 6, 1981

[54] NICKEL YLIDES

[75] Inventors: David L. Beach, Gibsonia; James J. Harrison, Glenshaw, both of Pa.

[73] Assignee: Gulf Research & Development Company, Pittsburgh, Pa.

[21] Appl. No.: 179,079

[22] Filed: Aug. 18, 1980

[51] Int. Cl.³ .............................................. C07F 15/04
[52] U.S. Cl. ................................ 260/439 R; 260/440; 260/446; 260/505 R; 260/543 P; 252/431 R; 252/431 N; 252/431 P; 568/9; 568/10; 568/11; 568/13; 568/14; 568/15; 568/16; 568/17
[58] Field of Search ..................................... 260/439 R

[56] References Cited

U.S. PATENT DOCUMENTS 2,998,416  8/1961  Mendel ............................... 260/93.7
3,686,159  8/1972  Bauer et al. .................... 260/94.9 C

OTHER PUBLICATIONS

Keim et al., "Agnew. Chem. Int. Ed. Engl.", vol. 17, No. 6, pp. 467-468, (1978).

Primary Examiner—Robert V. Hines
Attorney, Agent, or Firm—Forrest D. Stine; Joseph J. Carducci

[57] ABSTRACT

A new group of nickel ylides is provided that is highly active at relatively low operating temperatures and pressures in the oligomerization of ethylene. The compounds can be defined by the following Formula I:

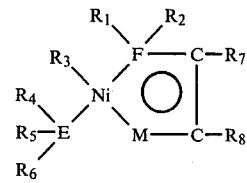

wherein $R_1$, $R_2$, $R_3$, $R_4$, $R_5$, $R_6$, $R_7$ and $R_8$ are either alike or different members selected from the group consisting of hydrogen, alkyl radicals having from about one to about 24 carbon atoms, preferably from about one to about 10 carbon atoms; aryl radicals having from about six to about 20 carbon atoms, preferably from about six to about 10 carbon atoms; alkenyl radicals having from about two to about 30 carbon atoms, preferably from about two to about 20 carbon atoms; cycloalkyl radicals having from about three to about 40 carbon atoms, preferably from about three to about 30 carbon atoms; aralkyl and alkaryl radicals having from about six to about 40 carbon atoms, preferably from about six to about 30 carbon atoms; a halogen radical selected from the group consisting of fluorine, chlorine, bromine and iodine, preferably chlorine; a hydroxyl group; an alkoxy or aryloxy group; and a hydrocarbyl group, such as defined above, carrying halogen, hydroxyl or alkoxy or aryloxy; provided that at least one, preferably from about one to about four, of each of $R_1$ to $R_8$ is a sulfonato group ($-SO_3^-$) or an alkyl, aryl, alkenyl, cycloalkyl, aralkyl or alkaryl group carrying a sulfonato group; M is sulfur or oxygen, preferably oxygen; E is phosphorus, arsenic, antimony or nitrogen, preferably phosphorus; and F is phosphorus, arsenic or antimony, preferably phosphorus.

19 Claims, No Drawings

NICKEL YLIDES

CROSS-REFERENCES TO RELATED APPLICATIONS

Reference is made to applicants' following U.S. applications:

U.S. Patent application Ser. No. 179,075, filed Aug. 18, 1980, entitled "Process for the Preparation of Nickel Ylides Containing Sulfonated Group V Ligands".

U.S. Patent application Ser. No. 179,080, filed Aug. 18, 1980, entitled "Process for the Preparation of Nickel Ylides Containing Ylide Ligands With a Sulfonated Group V Component".

U.S. Patent application Ser. No. 179,078, filed Aug. 18, 1980, entitled "Process for the Preparation of Nickel Ylides Containing Directly Sulfonated Ylide Ligands".

U.S. Patent application Ser. No. 179,076, filed Aug. 18, 1980, entitled "Process for Oligomerization of Alpha Olefins".

U.S. Patent application Ser. No. 179,005, filed Aug. 18, 1980, entitled "Process for the Oligomerization of Ethylene in Methanol".

The disclosures of the foregoing applications are hereby incorporated by reference.

FIELD OF THE INVENTION

The present invention relates to novel nickel ylides which are useful as catalysts for the oligomerization of ethylene.

DESCRIPTION OF THE PRIOR ART

It is well known in the art to use a variety of catalysts to oligomerize ethylene to higher molecular weight olefins. The term "oligomerize" has been employed, and is employed herein to describe the conversion of lower olefins such as ethylene to olefinic products of higher molecular weight, e.g., to dimer, trimer, tetramer and the like. The reaction rate and product distribution obtained are highly dependent on the exact catalyst composition and the reaction conditions employed. Two such general classes of catalysts are the "Ziegler" types consisting of aluminum trialkyls and the "Ziegler-Natta" types consisting of aluminum alkyls or alkyl halides and titanium halides. Major disadvantges of aluminum alkyl catalysts are their highly reactive and pyrophoric nature and the fact that they must be used at relatively high temperatures, e.g., 200°–275° C. and pressures, e.g., 2000–4000 psig (13,790 to 27,580 kPa). Although much milder reaction conditions are used when the aluminun alkyls are used in conjunction with titanium halides, product quality and ease of catalyst separation from products of both of these prior art types of catalysts are not as high as desired.

An article by W. Keim, F. H. Kowaldt, R. Goddard and C. Kruger entitled "Novel Coordination of (Benzoylmethylene)triphenylphosphorane in a Nickel Oligomerization Catalyst", in *Agnew. Chem. Int. Ed. Engl.* (1978) No. 6, page 466, discloses a nickel ylide having the structure:

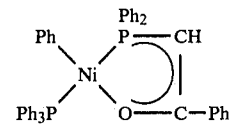

It is reported that this compound converts ethylene into alpha olefins or polyethylene.

SUMMARY OF THE INVENTION

A new group of nickel ylides has now been found that is highly active at relatively low operating temperatures and pressures in the oligomerization of ethylene. The compounds can be defined by the following Formula I:

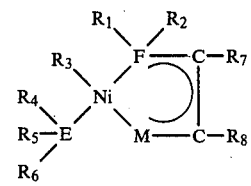

wherein $R_1$, $R_2$, $R_3$, $R_4$, $R_5$, $R_6$, $R_7$ and $R_8$ are either alike or different members selected from the group consisting of hydrogen, alkyl radicals having from about one to about 24 carbon atoms, preferably from about one to about 10 carbon atoms; aryl radicals having from about six to about 20 carbon atoms, preferably from about six to about 10 carbon atoms; alkenyl radicals having from about two to about 30 carbon atoms, preferably from about two to about 20 carbon atoms; cycloalkyl radicals having from about three to about 40 carbon atoms, preferably from about three to about 30 carbon atoms; aralkyl and alkaryl radicals having from about six to about 40 carbon atoms, preferably from about six to about 30 carbon atoms; a halogen radical selected from the group consisting of fluorine, chlorine, bromine and iodine, preferably chlorine; a hydroxyl group; an alkoxy or aryloxy group; and a hydrocarbyl group, such as defined above, carrying halogen, hydroxyl or alkoxy or aryloxy; provided that at least one, preferably from about one to about four, of each of $R_1$ to $R_8$ is a sulfonato group ($-SO_3^-$) or an alkyl, aryl, alkenyl, cycloalkyl, aralkyl or alkaryl group carrying a sulfonato group; M is sulfur or oxygen, preferably oxygen; E is phosphorus, arsenic, antimony or nitrogen, preferably phosphorus; and F is phosphorus, arsenic or antimony, preferably phosphorus. Specific examples of such nickel ylides are set forth in Table I. In this table and as used elsewhere herein, "Ph" represents phenyl and "Et" represents ethyl.

TABLE I

| Compound | $R_1$ | $R_2$ | $R_3$ | $R_4$ | $R_5$ | $R_6$ | $R_7$ | $R_8$ | E | F | M |
|---|---|---|---|---|---|---|---|---|---|---|---|
| 1 | Ph | Ph | Ph | Ph | Ph | Ph | $SO_3^-$ | Ph | P | P | O |
| 2 | Ph | Ph | Ph | Ph | Ph | Ph | H | Ph | P | P | O |
| 3 | Ph | Ph | Ph-$SO_3^-$ | Ph | Ph | Ph | H | Ph | P | P | O |
| 4 | Ph-$SO_3^-$ | Ph | Ph | Ph-$SO_3^-$ | Ph | Ph | H | Ph | P | P | O |
| 5 | Ph-$SO_3^-$ | Ph | Ph | Ph | Ph | Ph | H | Ph | P | P | O |
| 6 | Ph | Ph | Ph | Ph | Ph-$SO_3^-$ | Ph-$SO_3^-$ | $SO_3^-$ | Ph | P | P | O |
| 7 | Ph | Ph | Ph | Ph | Ph | Ph | $SO_3^-$ | Ph | As | P | O |
| 8 | Ph | Ph | Ph | Ph | Ph | Ph | $SO_3^-$ | Ph | P | P | S |
| 9 | Ph | Ph | Ph | $CH_2Ph$ | $CH_2Ph$ | $CH_2Ph$ | $SO_3^-$ | H | P | P | O |
| 10 | Ph | Ph | Ph | Ph | Ph | Ph | $SO_3^-$ | $CH_3$ | P | P | O |
| 11 | Ph | Ph | Ph | Ph | Ph | Ph | $SO_3^-$ | $Ph-Ph$ | P | P | O |
| 12 | Et | Et | Ph | Ph | Ph | Ph | H | Ph | P | P | O |
| 13 | Ph | Ph | Ph | Ph | Ph | Ph | H | Ph | P | P | O |
| 14 | Ph | Ph | Ph | Et | Et | Et | $SO_3^-$ | Ph | N | P | O |
| 15 | H | H | H | Ph | Ph | Ph | $SO_3^-$ | Ph | Sb | P | O |
| 16 | Ph | Ph | Ph | Ph | Ph | Ph | $SO_3^-$ | Ph | P | P | O |
| 17 | Ph | Ph | Ph | Ph-Cl | Ph-Cl | Ph-Cl | $(CH_2)_3CH_2-SO_3^-$ | Ph | P | P | O |
| 18 | H | H | H | Ph | Ph | Ph | $SO_3^-$ | Ph | P | P | O |
| 19 | Ph | Ph | Ph | Ph | Ph | Ph | $SO_3^-$ | Ph | P | P | O |
| 20 | Ph | Ph | Ph | Ph | Ph | Ph | Ph | $CH_3$ | P | As | S |
| 21 | Ph | Ph | Ph | Ph | Ph | Ph | H | $OCH_3$ | P | P | O |
| 22 | Ph | Ph | Ph | Ph | Ph | Ph | H | $OCH_3$ | P | P | O |
| 23 | Ph | Ph | Ph | Ph | Ph | Ph | $SO_3^-$ | OEt | As | P | O |
| 24 | Ph | Ph | Ph-$SO_3^-$ | Ph | Ph | Ph | H | $OC_4H_9$ | P | P | S |

TABLE I-continued

| Compound | $R_1$ | $R_2$ | $R_3$ | $R_4$ | $R_5$ | $R_6$ | $R_7$ | $R_8$ | E | F | M |
|---|---|---|---|---|---|---|---|---|---|---|---|
| 25 | $CH_3$ | $CH_3$ | $CH_3$ | Ph | Ph | Ph | $SO_3^-$ | $OCH_3$ | P | As | O |
| 26 | Ph | Ph | Ph | Ph | 4-$SO_3^-$-C$_6$H$_4$-Ph | Ph | H | 4-$O^-$-C$_6$H$_4$-$SO_3^-$ | P | P | O |
| 27 | Ph | 4-$SO_3^-$-C$_6$H$_4$-Ph | Ph | Ph | Ph | Ph | $SO_3^-$ | 4-$O^-$-C$_6$H$_4$-$SO_3^-$ | P | P | O |
| 28 | Ph | Ph | Ph | 4-$SO_3^-$-C$_6$H$_4$-Ph | Ph | Ph | H | $OC_3H_7$ | As | As | S |
| 29 | Ph | 4-$SO_3^-$-C$_6$H$_4$-Ph | Ph | cyclohexyl | Ph | Ph | H | $CH_3$ | P | As | O |
| 30 | Ph | Ph | Ph | cyclohexyl Et | cyclohexyl Et | cyclohexyl Et | $SO_3^-$ | $CH_3$ | As | P | O |
| 31 | $CH_3$ | $CH_3$ | $CH_3$ | Et | Et | Et | $SO_3^-$ | $OC_4H_9$ | P | P | O |
| 32 | $CH_3$ | $CH_3$ | $CH_3$ | 4-$SO_3^-$-C$_6$H$_4$-Ph | Ph | Ph | H | $OC_4H_9$ | P | P | O |
| 33 | Ph | $CH_3$ | $CH_3$ | $CH_3$ Ph | $CH_3$ Ph | $CH_3$ Ph | $SO_3^-$ | $CH_3$ | As | As | S |
| 34 | Ph | Ph | Ph | Ph | Ph | Ph | H | 4-$OCH_3$-C$_6$H$_4$-$CH_3$ | P | P | O |
| 35 | $CH_3$ | $CH_3$ | Ph | 4-$SO_3^-$-C$_6$H$_4$-Ph | Ph | Ph | $SO_3^-$ | 4-$OCH_3$-C$_6$H$_4$-$CH_3$ | As | As | S |
| 36 | H | Ph | Ph | H | Ph | H | $SO_3^-$ | H | P | P | O |
| 37 | Ph | Et | Et | Ph | Ph | Ph | $SO_3^-$ | $CH_3$ | As | As | S |
| 38 | Ph | H | H | H | H | H | $SO_3^-$ | H | P | P | O |
| 39 | 4-$OCH_3$-C$_6$H$_4$-Ph | 4-$OCH_3$-C$_6$H$_4$-Ph | 4-$OCH_3$-C$_6$H$_4$-Ph | Ph | Ph | butyl | $SO_3^-$ | $OCH_3$ | As | P | O |
| 40 | Ph | Ph | Ph | butyl | butyl | butyl | $SO_3^-$ | Ph | P | As | O |

When used to oligomerize ethylene the compounds of the present invention are characterized by a relatively high reaction rate at low temperatures and pressures. Their use results in the production of relatively high proportions of desirable trimer, tetramer, pentamer, and higher olefinic products. Additionally, they do not exhibit pyrophoric behavior and can be used at lower temperatures and pressures than conventional aluminum alkyl catalysts.

The presence of the sulfonato group in the nickel ylide catalysts of this invention induces solubility in polar solvents such as water or methanol. This allows conducting the catalytic reaction in a two-phase system to facilitate product removal and separation or the use of extractive techniques, e.g., by the use of aqueous ammonium hydroxide, not possible with the corresponding nickel ylides which do not contain a sulfonato group.

DESCRIPTION OF THE PREFERRED EMBODIMENTS

The novel nickel ylide compounds of this invention can be prepared using several different procedures. The following procedure, Procedure I, relates to the preparation of novel nickel ylides wherein the sulfonato group is located in $R_4$, $R_5$ and/or $R_6$ and at least one of $R_4$, $R_5$ and $R_6$ is aryl.

The first step in Procedure I involves sulfonating a ligand defined by the formula:

wherein $R_4$ to $R_6$ and E are as defined above, provided that at least one of $R_4$, $R_5$ and $R_6$ is an aryl group as defined above using $SO_3$ in the presence of a strong inorganic mineral acid, such as sulfuric acid, hydrochloric acid, nitric acid, phosphoric acid, etc. Specific examples of such ligands that can be used include: allyldiphenylphosphine; benzyldiphenylphosphine; bis(3-aminopropyl)phenylphosphine; bis(2-cyanoethyl)phenylphosphine; bis(m-fluorophenyl)phosphinous chloride; 4-bromophenyldiphenylphosphine; n-butyldiphenylphosphine; t-butyldiphenylphosphine; 2-cyanoethyldiphenylphosphine; cyclohexyldiphenylphosphine; n-decylphenylphosphine; diallylphenylphosphine; di-n-amylphenylphosphine; di-sec-butylphenylphosphine; dicyclohexylphenylphosphine; di-ethylphenylphosphine; di-n-heptylphenylphosphine; di-n-hexylphenylphosphine; dimethylphenylphosphine; dimethyl-p-tolylphosphine; diphenyl-n-butoxyphosphine; diphenylchlorophosphine; diphenylenephenylphosphine; diphenylethoxyphosphine; di-phenylmethoxyphosphine; diphenylphosphine; beta-diphenylphosphinoethyltriethoxysilane; di-iso-propylphenylphosphine; di-o- tolylphenylphosphine; divinylphenylphosphine; ethyldiphenylphosphine; n-hexyldiphenylphosphine; o-methoxyphenyldiphenylphosphine; (2-methylbutyl)diphenylphosphine; methyldiphenylphosphine; methylethylphenylphosphine; methylphenylphosphine; neomenthyldiphenylphosphine; pentafluorophenyldiphenylphosphine; (2-phenylbutyl)di-phenylphosphine; phenyldi-n-butoxyphosphine; phenyldichlorphosphine; phenyldiethoxyphosphine; phenyldimethoxyphosphine; phenylphosphine; isopropyldiphenylphosphine; n-propyldiphenylphosphine; o-tolyldiphenylphosphine; p-tolyldiphenylphosphine; tribenzylphosphine; tris(m-chlorophenyl)phosphine; tris(p-chlorophenyl)phosphine; tri(1-naphthyl)-phosphine; triphenylphosphine; tris(4-dimethylaminophenyl)phosphine; tris(p-fluorophenyl)phosphine; tris(o-methoxyphenyl)phosphine; tris(p-methoxyphenyl)phosphine; tri-o-tolylphosphine; tri-m-tolylphosphine; tri-p-tolylphosphine; vinyldiphenylphosphine; sodium diphenylphosphinebenzene-3-sulfonate; disodium phenylphosphine bis(benzene-3-sulfonate); dimethylphenylarsine; methyldiphenylarsine; triphenylarsine; tri-p-tolylarsine; di-phenylchloroarsine; triphenylantimony; triphenylamine; tribenzylamine; methyldiphenylamine; and dimethylphenylamine.

It is preferred to use fuming sulfuric acid ($H_2SO_4$.$XSO_3$, where x can be, for example, from about 0.1 to about 0.6, preferably from about 0.2 to about 0.4). The amount of $SO_3$ is not critical and can vary over a wide range, for example, at least about one mole per mole of ligand, preferably from about two to about 20 moles per mole of ligand. The two reactants are stirred and heated at a temperature of about 0° to about 200° C., preferably about 40° to about 100° C., for about one minute to about 48 hours, preferably for about 30 minutes to about four hours. Any suitable pressure can be used, although atmospheric pressure is preferred. At the end of this period the reactor contents are cooled to a temperature of about −30° to about 50° C., preferably about room temperature (about 26° C.), after which sufficient water and a suitable base, such as an alkaline metal hydroxide, an alkali metal alkoxide, ammonium hydroxide, a hydrocarbyl-substituted ammonium hydroxide, etc. are added thereto to crystallize the sulfonated ligand out of solution. For example, the amount of water used can range from about 10 milliliters to about 10 liters per mole of sulfonated ligand. The crystals can be recovered in any suitable manner, for example, by filtration, decantation or by centrifuging.

In the second step of Procedure I, the sulfonated ligand obtained in the first step is reacted with any zero valent nickel compound, or any nickel compound convertible to a zero valent nickel compound in situ, and a ylide defined by the following Formula II:

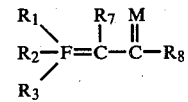

wherein $R_1$, $R_2$, $R_3$, $R_7$, $R_8$, M and F are as defined above. Specific examples of such nickel compounds which can be used include: tris(triphenylphosphine)nickel; bis(cyclooctadiene)nickel; tetrakis(triphenylphosphine)nickel; bis(norbornadiene)nickel; (cycloocta-1,5-diene)duroquinone nickel; (dicyclopentadiene)duroquinone nickel; bis(tetracyclone)nickel; tetrakis(triethylphosphine)nickel; tris(triethylphosphine)nickel; bis(triphenylphosphine)nickel dicarbonyl; nickel carbonyl; nickel(II)acetylacetonate; nickelocene; bis(triethylphosphine)nickel(II)chloride; tetrakis(trifluorophosphine)nickel; nickel acetate; nickel bromide; nickel carbonate; nickel chloride; nickel fluoride; nickel iodide; nickel nitrate, nickel sulfate; nickel 2,4-pentanedionate; bis π-allyl nickel; and nickel di-chloride hexaamine. Specific examples of ylides coming within the definition of Formula II are set forth in Table II.

TABLE II

| Compound | R₁ | R₂ | R₃ | R₇ | R₈ | F | M |
|---|---|---|---|---|---|---|---|
| 1 | Ph | Ph | Ph | H | Ph | P | O |
| 2 | Ph | Ph | Ph | H | Ph | P | S |
| 3 | Ph | Ph | Ph | SO₃⁻ | Ph | P | O |
| 4 | Ph | Ph | Ph | SO₃⁻ | Ph | P | S |
| 5 | 4-SO₃⁻-C₆H₄- | Ph | Ph | H | Ph | P | O |
| 6 | Ph | 4-SO₃⁻-C₆H₄- | Ph | SO₃⁻ | Ph | P | S |
| 7 | Ph | Ph | Ph | H | OCH₃ | P | O |
| 8 | Ph | Ph | Ph | SO₃⁻ | OCH₃ | R | O |
| 9 | Ph | Ph | Ph | H | OCH₃ | P | S |
| 10 | 4-SO₃⁻-C₆H₄- | Ph | Ph | H | OCH₃ | P | O |
| 11 | Ph | 4-SO₃⁻-C₆H₄- | Ph | SO₃⁻ | OCH₃ | P | O |
| 12 | Ph | Ph | Ph | H | CH₃ | P | O |
| 13 | Ph | Ph | Ph | SO₃⁻ | OCH₃ | P | O |
| 14 | 4-SO₃⁻-C₆H₄- | Ph | Ph | H | CH₃ | P | O |
| 15 | Ph | 4-SO₃⁻-C₆H₄- | Ph | SO₃⁻ | CH₃ | P | O |
| 16 | Ph | Ph | Ph | SO₃⁻ | CH₃ | P | S |
| 17 | Ph | Ph | Ph | H | CH₃ | P | O |
| 18 | CH₃ | CH₃ | CH₃ | H | Ph | P | O |
| 19 | CH₃ | CH₃ | CH₃ | SO₃⁻ | Ph | P | O |
| 20 | CH₃ | CH₃ | CH₃ | H | Ph | P | S |
| 21 | CH₃ | CH₃ | CH₃ | SO₃⁻ | Ph | P | S |
| 22 | Et | Et | Et | SO₃⁻ | Ph | P | O |
| 23 | CH₃ | 4-SO₃⁻-C₆H₄- | Et | H | Ph | P | O |
| 24 | CH₃ | Cyclohexyl | Ph | SO₃⁻ | Ph | P | S |
| 25 | CH₃ | CH₃ | CH₃ | H | OCH₃ | P | O |
| 26 | CH₃ | Ph | Et | SO₃⁻ | CH₃ | P | O |
| 27 | 4-SO₃⁻-C₆H₄- | Ph | Et | H | OCH₃ | P | S |
| 28 | CH₃ | CH₃ | CH₃ | H | CH₃ | P | O |
| 29 | Ph | CH₃ | Et | SO₃⁻ | CH₃ | P | O |
| 30 | Ph | 4-SO₃⁻-C₆H₄- | CH₃ | H | CH₃ | P | S |
| 31 | Ph | Ph | Et | SO₃⁻ | CH₃ | P | S |
| 32 | 4-SO₃⁻-C₆H₄- | CH₃ | Et | SO₃⁻ | CH₃ | P | O |
| 33 | 4-Cl-C₆H₄- | Ph | Ph | SO₃⁻ | Ph | P | O |
| 34 | 4-Cl-C₆H₄- | Ph | CH₃ | H | Ph | P | S |
| 35 | CH₃ | CH₃ | Et | SO₃⁻ | 4-Cl-C₆H₄- | P | O |
| 36 | Ph | Ph | Ph | H | Ph | As | O |
| 37 | Ph | Ph | Ph | H | Ph | As | S |
| 38 | Ph | Ph | Ph | SO₃⁻ | Ph | As | O |
| 39 | Ph | Ph | Ph | SO₃⁻ | CH₃ | As | O |
| 40 | CH₃ | CH₃ | CH₃ | H | Ph | As | O |
| 41 | Ph | CH₃ | CH₃ | SO₃⁻ | Ph | As | O |
| 42 | Ph | 4-SO₃⁻-C₆H₄- | CH₃ | H | Ph | As | O |
| 43 | Ph | Ph | Ph | H | Ph | Sb | O |
| 44 | Ph | Ph | Ph | SO₃⁻ | Ph | Sb | O |

TABLE II-continued

| Compound | R₁ | R₂ | R₃ | R₇ | R₈ | F | M |
|---|---|---|---|---|---|---|---|
| 45 | Ph | -⌬-SO₃⁻ | Ph | H | Ph | Sb | O |
| 46 | Ph | -⌬-SO₃⁻ | Ph | SO₃⁻ | Ph | Sb | O |
| 47 | Ph | Ph | Ph | H | Ph | Sb | O |
| 48 | Ph | Ph | Ph | SO₃⁻ | Ph | Sb | S |
| 49 | CH₃ | CH₃ | CH₃ | H | Ph | Sb | O |
| 50 | CH₃ | Ph | CH₃ | SO₃⁻ | Ph | Sb | O |
| 51 | Ph | Ph | Ph | H | O-⌬-SO₃⁻ | P | O |
| 52 | Ph | Ph | Ph | H | O-⌬-SO₃⁻ | P | S |
| 53 | Ph | -⌬-SO₃⁻ | Ph | H | OC₃H₇ | P | O |
| 54 | Ph | Ph | Ph | SO₃⁻ | OC₄H₉ | P | O |
| 55 | Ph | Ph | Ph | SO₃⁻ | O-⌬-SO₃⁻ | P | O |
| 56 | Ph | Ph | Ph | H | O-⌬-SO₃⁻ | As | O |

In this second step approximately equal molar amounts of each of the three reactants defined above are dissolved in any suitable unreactive solvent, such as toluene, tetrahydrofuran, dioxane, or other unreactive hydrocarbon solvents, and stirred while maintaining a temperature of about 0° to about 100° C., preferably room temperature, for about one-half hour to about 48 hours, preferably about three to about 20 hours, sufficient to ensure complete reaction. Any suitable pressure can be used, although atmospheric pressure is preferred. The solvent can be removed from the reaction mixture in any suitable manner, for example, by distillation, including vacuum distillation, if necessary, leaving behind the novel compound defined above. On the other hand, a second solvent in which the desired product is insoluble, such as heptane, can be added to the reaction product to precipitate the novel compound therein. The novel compound can be recovered, for example, by filtration, decantation or by centrifuging.

The following procedure, Procedure II, relates to the preparation of novel nickel ylides wherein the sulfonato group is located in R₁, R₂, and/or R₃. In this procedure, the first step involves reacting a ligand, defined by the formula:

wherein R₁, R₂, R₃ and F are as defined above, provided that at least one of R₁, R₂ and R₃ is a sulfonato group or an alkyl, aryl, alkenyl, cycloalkyl, aralkyl or alkaryl, as defined above, carrying a sulfonato group, with an alpha substituted ketone or aldehyde or an alpha substituted thioketone or thioaldehyde defined by the following formula:

$$\overset{M}{\underset{H}{R_8-C-\overset{X}{C}-R_7}}$$

wherein R₇, R₈ and M are as defined above and X is a halogen radical selected from the group consisting of fluorine, chlorine, bromine and iodine, preferably chlorine and bromine, a tosyl group (a toluene sulfonate group), or an acetate group. The sulfonated ligand can be obtained in any conventional manner by sulfonating the appropriate trihydrocarbyl phosphine, arsine or stibine or by sulfonating using the procedure employed in Procedure I. Specific examples of ligands that can be used include: allyldiphenylphosphine; benzyldiphenylphosphine; bis(3-aminopropyl)phenylphosphine; bis(2-cyanoethyl)phenylphosphine; bis(m-fluorophenyl)phosphinous chloride; 4-bromophenyldiphenylphosphine; n-butyldiphenylphosphine, t-butyldiphenylphosphine; 2-cyanoethyldiphenylphosphine; cyclohexyldiphenylphosphine; n-decylphenylphosphine; diallylphenylphosphine; di-n-amylphenylphosphine; di-sec-butylphenylphosphine; di-cyclohexylphenylphosphine; di-ethylphenylphosphine; di-n-heptylphenylphosphine; di-n-hexylphenylphosphine; di-methylphenylphosphine; dimethyl-p-tolylphosphine; di-phenyl-n-butoxyphosphine; diphenylchlorophosphine; di-phenylenephenylphosphine; diphenylethoxyphosphine; di-phenylmethoxyphosphine; diphenylphosphine; beta-diphenylphosphinoethyltriethoxysilane; di-iso-propylphenylphosphine; di-o-tolylphenylphosphine; divinylphenylphosphine; ethyldiphenylphosphine; n-hexyldiphenylphosphine; o-methoxyphenyldiphenylphosphine; (2-methylbutyl)diphenylphosphine; methyldiphenylphosphine; methylethylphenylphosphine; methylphenylphosphine; neomenthyldiphenylphosphine; pentafluorophenyldiphenylphosphine; (2-phenylbutyl)diphenylphosphine; phenyldi-n-butoxyphosphine; phenyldichlorophosphine; phenyldiethoxyphosphine; phenyldimethoxyphosphine; phenylphosphine; isopropyldiphenylphosphine; n-propyldiphenylphosphine; o-tolyldiphenylphosphine; p-tolyldiphenylphosphine; tribenzylphosphine; tris(m-chlorophenyl)phosphine; tris(p-chlorophenyl)phosphine; tris(1-naphthyl)phosphine; triphenylphosphine; tris(4-dimethylaminophenyl)phosphine; tris(p-fluorophenyl)phosphine; tris(o-methoxyphenyl)phosphine; tris(p-methoxyphenyl)phosphine; tri-o-tolylphosphine; tri-m-tolylphosphine; tri-p-tolylphosphine; vinyldiphenylphosphine; sodium diphenylphosphinebenzene-3-sulfonate; disodium phenylphosphinebis(benzene-3-sulfonate); dimethylphenylarsine; methyldiphenylarsine; triphenylarsine; tri-p-tolylarsine; diphenylchloroarsine; and triphenylantimony. Specific examples of such alpha substituted ketones or aldehydes and of alpha substituted thioketones or thioaldehydes that can be used herein include: phenacylchloride; phenacylbromide; alphaacetoxyacetophenone; alpha-bromo-2'-acetonaphthone; alpha-bromoacetone; 3-bromocamphor; alpha-bromo-p-chloroacetophenone; alpha-bromo-2',4'-dimethoxyacetophenone; alphabromoiosbutyrophenone; alpha-bromo-o-methoxyacetophenone; alpha-bromo-m-methoxyacetophenone; alpha-bromo-p-methoxyacetophenone; alpha-bromo-4'-methylacetophenone; p-bromophenacrylbromide; alpha-bromopropiophenone; chloroacetone; alpha-chloro-p-fluoroacetophenone; alpha-chlorobutyrophenone; p-chlorophenacylchloride; alpha-chloropropiophenone; alpha-chlorothioacetophenone; alpha-bromothioacetophenone; alpha-chloroethylnaphthylketone; alphachloromethylacetate; alpha-bromomethylacetate; alphachloroethylacetate; alphabromoethylacetate; alpha-chloropropylacetate; alphachlorobutylacetate; alpha-chlorophenylacetate; alphachloro-p-sulfonatophenylacetate; alpha-bromopropylacetate; alpha-bromobutylacetate; alpha-bromophenylacetate; and alpha-bromo-p-sulfonatophenylacetate.

The reaction between the sulfonated ligand and the ketone or aldehyde is carried out using about equal molar amounts of each reactant while they are dissolved in an appropriate hydrocarbon solvent, such as toluene or tetrahydrofuran, and the reaction is carried out at a temperature of about 20° to about 200° C., preferably about 50° to about 150° C., and any suitable pressure, preferably atmospheric, for about one to about 24 hours, preferably for about two to about eight hours. The reaction mixture is then cooled, preferably to room temperature. If a solid results from such cooling it is recovered in any suitable manner, for example, by filtration, decantation or by centrifuging. If solids do not form, the reaction mixture can be subjected to distillation to remove solvents therefrom, leaving behind novel solid material, which is a salt defined by the following Formula III:

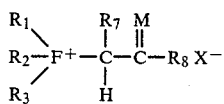

wherein $R_1$, $R_2$, $R_3$, $R_7$, $R_8$, F, M and X are as defined in the previous paragraph.

To convert the above salt to the corresponding ylide, the salt is reacted with a stoichiometric amount of a base, such as an alkali metal hydroxide (sodium or potassium hydroxide), an alkyl or aryl lithium (n-butyl lithium, methyl lithium or phenyl lithium), an alkoxide (sodium methoxide or potassium t-butoxide), a hydrocarbylsubstituted ammonium hydroxide (benzyltrimethylammonium hydroxide), ammonium hydroxide, ammonia, etc. This can be done, for example, by suspending or dissolving the salt in a suitable liquid, such as water, an alcohol (ethanol or isopropanol), an aromatic (benzene or toluene), a hydrocarbon (hexane or heptane), etc. The reaction temperature can range from about room temperature to about 200° C., preferably from about room temperature to about 50° C., and the reaction time from about one minute to about four hours, or even longer, but preferably from about one to about two hours. Elevated pressures can be used, although atmospheric pressure will suffice. If the ylide obtained is a solid, recovery can be effected by filtration, decantation or by centrifuging. If the ylide is dissolved in the solvent, simple distillation is sufficient to remove the solvent, leaving behind the solid ylide. In some cases in association with the ylide so recovered will be the salt corresponding to the base that was used. For example, use of sodium hydroxide produces the corresponding sodium salt. The salt and the desired ylide can be separated from each other in any convenient manner, for example, by extraction with a solvent that will dissolve one and not the other. For example, aromatics, such as toluene, can be used to dissolve the ylide, while water can be used to dissolve the salt. The novel ylide obtained can be defined by the following Formula IV:

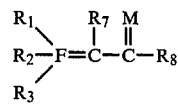

wherein $R_1$, $R_2$, $R_3$, $R_7$, $R_8$, F and M are as defined in Formula III.

The above identified ylide (Formula IV) is then reacted with (1) a ligand defined by the formula:

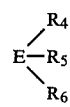

where $R_4$, $R_5$, and $R_6$ can be a hydrocarbyl, as defined above, a sulfonated hydrocarbyl or a sulfonato group, and E is as defined above; and (2) a zero valent nickel compound, following the procedure of Procedure I. Specific examples of ligands that can be used include: allyldiphenylphosphine; benzyldiphenylphosphine; bis(3-aminopropyl) phenylphosphine; bis(2-cyanoethyl)phenylphosphine; bis(m-fluorophenyl)phosphinous chloride; 4-bromophenyldiphenylphosphine; n-butyldiphenylphosphine; t-butyldiphenylphosphine; 2-cyanoethyldiphenylphosphine; cyclohexyldiphenylphosphine; n-decylphenylphosphine; diallylphenylphosphine; di-n-amylphenylphosphine; di-sec-butylphenylphosphine; dicyclohexylphenylphosphine; diethylphenylphosphine; di-n-heptylphenylphosphine; di-n-hexylphenylphosphine; di-methylphenylphosphine; dimethyl-p-tolylphosphine; di-phenyl-n-butoxyphosphine; diphenylchlorophosphine; di-phenylenephenylphosphine; diphenylethoxyphosphine; di-phenylmethoxyphosphine; diphenylphosphine; beta-diphenylphosphinoethyltriethoxysilane; di-iso-propylphenylphosphine; di-o-tolylphenylphosphine; divinylphenylphosphine; ethyldiphenylphosphine; n-hexyldiphenylphosphine; o-methoxyphenyldiphenylphosphine; (2-methylbutyl)diphenylphosphine; methyldiphenylphosphine; methylethylphenylphosphine; methylphenylphosphine; neomenthyldiphenylphosphine; pentafluorophenyldiphenylphosphine; (2-phenylbutyl)diphenylphosphine; phenyldi-n-butoxyphosphine; phenyldichlorophosophine; phenyldiethoxyphosphine; phenyldimethoxyphosphine; phenylphosphine; isopropyldiphenylphosphine; n-propyldiphenylphosphine; o-tolyldiphenylphosphine; p-tolyldiphenylphosphine; tribenzylphosphine; tris(m-chlorophenyl)phosphine; tris(p-chlorophenyl)phosphine; tri(1-naphthyl)phosphine; triphenylphosphine; tris(4-dimethylaminophenyl)phosphine; tris(p-fluorophenyl)phosphine; tris-(o-methoxyphenyl)phosphine; tris(p-methoxyphenyl)phosphine; tri-o-tolylphosphine; tri-m-tolylphosphine; tri-p-tolylphosphine; vinyldiphenylphosphine; sodium diphenylphosphinebenzene-3-sulfonate; disodium phenylphosphinebis(benzene-3-sulfonate); dimethylphenylarsine; methyldiphenylarsine; triphenylarsine; tri-p-tolylarsine; diphenylchloroarsine; triphenylantimony; triphenylamine; tribenzylamine; methyldiphenylamine; dimethylphenylamine; bis(2-cyanoethyl)phosphine; bis(dimethylamino)methylphosphine; t-butyldichlorophosphine; 2-cyanoethylphosphine; cyclohexylphosphine; di-t-butylchlorophosphine; dicyclohexylphosphine; diethylethoxyphosphine; diethyl-iso-propoxyphosphine; diethylphosphine; triallylphosphine; triisobutylphosphine; tri-n-butylphosphine; tri-sec-butylphosphine; tri-t-butylphosphine; triethylphosphine; tri-n-hexylphosphine; trimethylphosphine; trifluorophosphine; tri-iso-propylphosphine; tri-n-propylphosphine; tris(2-cyanoethyl)phosphine; tris(dimethylamino)phosphine; tris(trimethylsilyl)phosphine; tri-n-butylantimony; triethylarsine; trimethylarsine; methyldiiodoarsine; trimethylamine; triethylamine; tributylamine; tripropylamine; dimethylamine; di-n-hexylamine; dicyclohexylamine; diethylamine; tricyclohexylamine; ammonia; and phosphine.

The following procedure, Procedure III, relates to the preparation of novel nickel ylides wherein the sulfonato group is in $R_7$. In the first step, the ylide defined by the following Formula V:

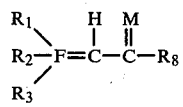

wherein each of $R_1$, $R_2$, $R_3$, and $R_8$ are hydrocarbyl radicals as defined above, and each of F and M is an element as defined above, is sulfonated to obtain the following sulfonated ylide defined by the following Formula VI:

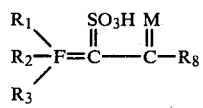

wherein each of $R_1$, $R_2$, $R_3$, $R_8$, M and F is as defined in Formula V. In some cases, for example, where $R_1$, $R_2$, $R_3$ and $R_8$ are phenyl, M is oxygen and F is phosphorus the following Formula VII may more accurately describe the structure:

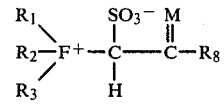

This first step can be done, for example, by dissolving the ylide of Formula V in a suitable solvent, for example, a halogenated hydrocarbon, such as chloroform, dichloroethane, methylene chloride or methyl chloroform, or a hydrocarbon solvent, such as heptane or hexane and then adding $SO_3$ to the resulting solution. The ylide and sulfonating agent are generally employed in equal molar amounts, although excess sulfonating agent can be present, if desired. Temperatures can be in the range of about 0° to about 200° C., preferably from about 20° to about 100° C., pressures can be elevated, although atmospheric pressure is preferred, and reaction times can vary from about five minutes to about 24 hours, preferably from about ten minutes to about four hours.

At the end of the reaction time the compounds defined by Formula VI or VII are recovered by any suitable means. If the sulfonated desired product is solid, recovery can be effected by filtration, decantation or by centrifuging. If the desired product is dissolved in the reaction medium, recovery can be effected by distillation to remove the solvent therefrom.

The sulfonated product is converted to the corresponding ylide by reacting the same with a base, such as an alkali metal hydroxide (sodium or potassium hydroxide), an alkyl or aryl lithium (n-butyl lithium, methyl lithium or phenyl lithium), an alkoxide (sodium methoxide or potassium t-butoxide), a hydrocarbyl-substituted ammonium hydroxide (benzyltrimethylammonium hydroxide), ammonium hydroxide, ammonia, etc., to produce the following ylide defined by Formula VIII:

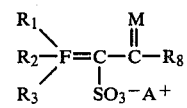

wherein $R_1$, $R_2$, $R_3$, $R_8$, F and M are as defined in Formula VI and A is the cationic portion of the base used. This can be done, for example, by suspending or dissolving the sulfonated ylide in a suitable liquid, such as water, an alcohol (ethanol or isopropanol), an aromatic (benzene or toluene), a hydrocarbon (hexane or heptane), etc. The reaction temperature can range from about room temperature to about 200° C., preferably from about room temperature to about 50° C., and the reaction time from about one minute to about four hours, or even longer, but preferably from about one to about two hours. Elevated pressures can be used, although atmospheric pressure will suffice. If the ylide obtained is a solid, recovery can be effected by filtration, decantation or by centrifuging. If the ylide is dissolved in the solvent, simple distillation is sufficient to remove the solvent, leaving behind the solid ylide.

The sulfonated ylide defined by Formula VIII is then reacted with (1) a ligand defined by the formula:

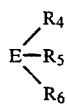

wherein R₄, R₅, and R₆ can be hydrocarbyl, as defined above, a sulfonated hydrocarbyl or a sulfonato group, and E is as defined above; and (2) a zero valent nickel compound, following the procedure of Procedure I. Specific examples of ligands that can be used include those previously set forth in Procedure II as examples of the ligand:

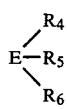

The novel nickel ylides produced herein, defined generically by Formula I, can be employed to oligomerize ethylene. This can be done, for example, by dissolving the nickel ylide in an appropriate solvent, such as toluene, dioxane, tetrahydrofuran, anisole, methanol, etc., such that the concentration therein will be in the range of about 0.0001 to about 10 moles per liter of solvent, preferably from about 0.001 to about 1.0 mole per liter of solvent. In certain modifications of the process, a portion of the oligomer product can suitably serve as at least a part of the reactor diluent. Ethylene is then added to the reaction zone and pressure is maintained therein within the range of about 10 to about 5000 pounds per square inch gauge (about 70 to about 35,000 kPa), preferably about 50 to about 1200 pounds per square inch gauge (about 350 to about 8400 kPa). Its concentration in the solution will be in the range of about 0.001 to about 20 moles per liter, preferably about 0.01 to about 10 mole per liter. The temperature is maintained between about −20° to about 200° C., preferably about 30° to about 150° C., while the reaction time can be from about 10 minutes to about 72 hours, but preferably from about one to about eight hours. During the reaction, the reaction mixture is stirred.

Solvent can be removed from the remaining product by any convenient means, for example, distillation, extraction or absorption, after which the olefinic oligomers can also be recovered by distillation or extraction, leaving behind the nickel ylide catalyst. After removing the unreacted olefin from the solvent mixture, the product can be extracted with a polar solvent, such as ammonium hydroxide or water, to remove nickel ylide, catalyst or catalyst residues therefrom. Separation of solvent from oligomer can be effected in a suitable manner, for example, by distillation. If the reaction is carried out in an appropriate polar solvent, such as methanol, the reaction mixture will resolve itself into a lower solvent therein, and an upper layer composed of small amounts of solvent and the oligomer. In such case, after removing unreacted olefin, the two layers are separated from each other, for example, by decantation, and the oligomer and solvent can be separated from each other as previously described.

The following examples illustrate the invention, and are not intended to limit the invention, but rather, are presented for purposes of illustration.

EXAMPLE I

This example is illustrative of Procedure I. To 20 milliliters of 30 percent fuming sulfuric acid there were added slowly with cooling 10 grams of triphenylphosphine. The solution was then heated to 80° C. and every five minutes the solution was tested by adding one drop of the solution to water until a clear solution was obtained. The reaction mixture was cooled to room temperature, poured into 200 cc of water and neutralized with 10 percent aqueous sodium hydroxide. After setting the solution overnight at room temperature, the desired product separated by crystallization and was recovered by filtration. The recovered product, sodium diphenylphosphinobenzene-3-sulfonate has the following structure:

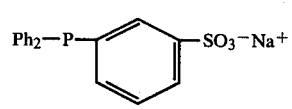

(Compound 1)

To 1.40 grams of bis(cyclooctadiene)nickel (5.1 millimoles) in 30 milliliters of toluene under an argon atmosphere there was added a solution of 1.86 grams of Compound 1 (5.1 millimoles) and 1.94 grams (5.1 millimoles) of benzoylmethylenetriphenylphosphorane:

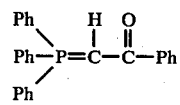

(Compound 2)

in 20 milliliters of toluene. After stirring for 18 hours at room temperature, the reaction mixture was heated to 50° C. to remove the solvent under a reduced pressure of 10 to 100 millimeters of mercury. The reaction mixture was transferred to an argon filled dry box and dissolved in toluene. Hexane was added to precipitate the product identified below as novel Compound 3. A total of 3.13 grams in 76 percent yield of the compound was recovered.

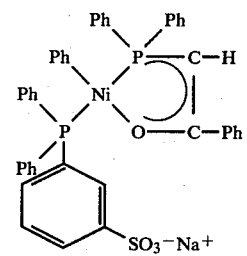

(Compound 3)

EXAMPLE II

This example is illustrative of Procedure II. To 4.65 grams of alpha-chloroacetophenone (0.03 mole) in 150 milliliters of toluene there were added 10.92 grams of Compound 1, (0.03 mole). This was heated to reflux under argon for five hours and then cooled and filtered. A total of 14.52 grams of the novel phosphonium salt:

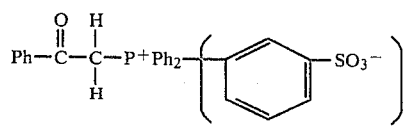
(Compound 4)

was obtained which was suspended in ethanol/water and titrated with 10 percent sodium hydroxide to a phenolphthalein end point. The ethanol was removed in vacuo and the product was washed with toluene to remove a small amount of unsubstituted benzoylmethylene triphenylphosphorane (1.2 grams). A total of 12.89 grams of the following novel phosphonium compound:

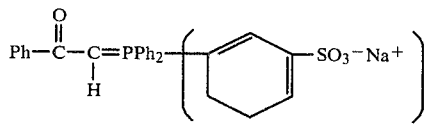
(Compound 5)

was obtained in 89 percent yield.

To 1.38 grams of bis(cyclooctadiene)nickel (five millimoles) in 70 milliliters of tetrahydrofuran there was added a mixture of 1.31 grams of triphenylphosphine (five millimoles) and 2.41 grams of Compound 5 (five millimoles) dissolved in 70 milliliters of tetrahydrofuran. This was stirred at room temperature for 18 hours, after which the solvent was removed in vacuo. The resulting product was dissolved in toluene and filtered. Heptane was then added to precipitate the following novel nickel ylide:

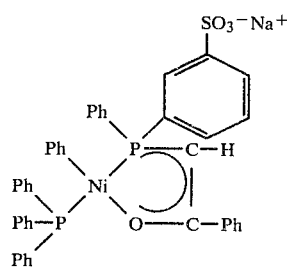
(Compound 6)

EXAMPLE III

This example is illustrative of Procedure III. To 4.01 grams of pyridine (0.05 mole) in 250 milliliters of dichloroethane there was added 6.97 grams of sulfur trioxide (0.087 mole) at 0° C. under nitrogen. After stirring for 0.5 hour, a solution of 19.05 grams of unsubstituted benzoylmethylenetriphenylphosphorane (0.05 mole) in 200 milliliters of dichloroethane was added. This was then heated to reflux for one hour. The reaction mixture was cooled to room temperature and the solvent removed in vacuo. The resulting product was then suspended in ethyl alcohol and filtered to give 19.7 grams of a white solid of the following phosphonium salt in 86 percent yield:

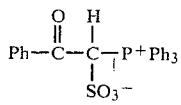
(Compound 7)

Compound 7 was also prepared as follows. To 29 grams of benzoylmethylenetriphenylphosphorane (0.076 mole) in 500 milliliters of dichloroethane at 25° C. under nitrogen there was added 5.47 milliliters of sulfur trioxide (0.132 mole). After stirring for 18 hours the solvent was removed in vacuo. Then 450 milliliters of ethanol and 50 milliliters of water were added and the mixture stirred for one-half hour. The product was filtered and washed with ether to give 31.8 grams, 87 percent yield, of Compound 7.

Compound 7 was then suspended in water and titrated with 10 percent aqueous sodium hydroxide to a phenolphthalein end point. The water was then removed in vacuo and final traces removed via ethanol azeotrope to give 20.7 grams of the following novel ylide in 86 percent yield:

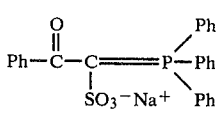
(Compound 8)

The novel nickel ylide, defined below as Compound 9, was prepared as follows. To 1.38 grams of bis(cyclooctadiene)nickel (five millimoles) in 30 milliliters of tetrahydrofuran there was added a mixture of 1.31 grams of triphenylphosphine (five millimoles) and 2.41 grams of Compound 8 (five millimoles) dissolved in 70 milliliters of tetrahydrofuran. The reaction mixture was stirred for 18 hours at room temperature, after which solvent was removed in vacuo. The resulting solid was dissolved in toluene and filtered. A yellow solid, which precipitated upon addition of heptane, was recovered by filtration. A total yield of 3.65 grams of Compound 9 was recovered in 91 percent yield.

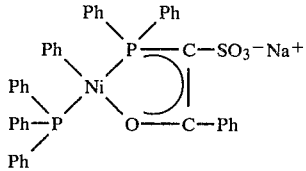
(Compound 9)

When Example III above was repeated except that Compound 7 was titrated with potassium hydroxide, ammonium hydroxide and trimethylphenylammonium hydroxide in place of 10 percent aqueous sodium hydroxide the following novel nickel ylides, respectively, were obtained:

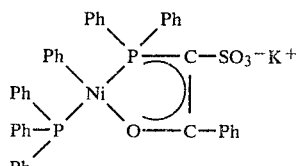
(Compound 10)

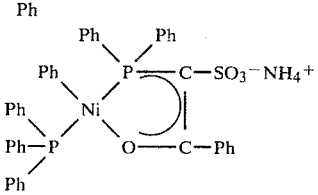
(Compound 11)

-continued

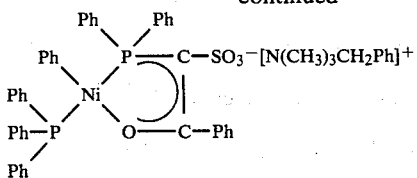
(Compound 12)

In producing Compounds 10, 11 and 12 identified above, it is apparent that the following ylides corresponding to Compound 8, respectively, will also be obtained:

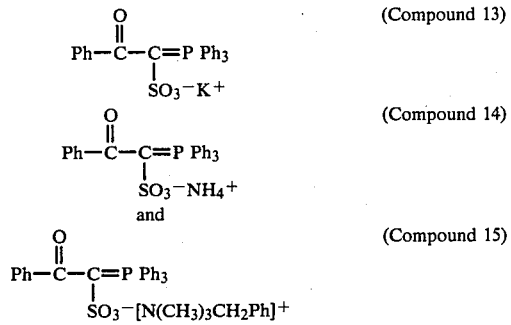

(Compound 13)

(Compound 14)

and (Compound 15)

EXAMPLE IV

Several runs were carried out wherein in each instance there was charged 0.1 millimole of sulfonated nickel ylide catalyst compounds 3, 6 and 9, each dissolved in 100 milliliters of toluene. During the reactions precautions were taken to exclude air contamination by performing the reactions in an argon atmosphere. The reaction mixture was then heated to 50° C. and pressured with ethylene to obtain a partial pressure thereof of 200 pounds per square inch gauge (1400 kPa). The reaction mixture was stirred throughout the reaction period of two hours, during which time the temperature and pressure were maintained constant. At the end of the two-hour period the reaction mixture was cooled to room temperature and unreacted ethylene removed therefrom by distillation. The amount of oligomer produced was determined and compared with the activity for the compound reported by the Keim et al article previously discussed. The results obtained are set forth in Table III.

TABLE III

| Run No. | Nickel Ylide Catalyst | Activity: Moles Ethylene Converted Per Mole of Nickel Catalyst |
|---|---|---|
| I | Keim et al specific catalyst | 6,000* |
| II | Compound 3 | 2,087 |
| III | Compound 6 | 6,965 |
| IV | Compound 9 | 20,022 |

*Reported by Keim et al

Each of Compounds 6 and 9 is more active than the unsulfonated nickel ylide of Keim et al. An additional advantage of each of Compounds 3, 6 and 9 over that of Keim et al lies in their easy recovery from the reaction product.

EXAMPLE V

An additional series of runs were carried out similar to Run No. IV but wherein the reactions were carried out at specific elevated temperatures. These data are summarized below in Table IV.

TABLE IV

| Run No. | Temperature, °C. | Activity: Moles Ethylene Converted Per Mole of Nickel Catalyst |
|---|---|---|
| IV | 50 | 20,022 |
| V | 70 | 16,811 |
| VI | 90 | 3,123 |
| VII. | 120 | 3,814 |
| VIII | 150 | 816 |

Although the invention has been described in considerable detail with particular reference to certain preferred embodiments thereof, variations and modifications can be effected within the spirit and scope of the invention as described hereinbefore, and as defined in the appended claims.

We claim:

1. A nickel ylide defined by the following formula:

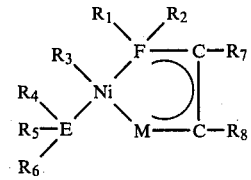

wherein $R_1$, $R_2$, $R_3$, $R_4$, $R_5$, $R_6$, $R_7$ and $R_8$ are either alike or different members selected from the group consisting of hydrogen, alkyl radicals having from about one to about 24 carbon atoms, aryl radicals having from about six to about 20 carbon atoms, alkenyl radicals having from about two to about 30 carbons atoms, cycloalkyl radicals having from about three to about 40 carbon atoms, aralkyl and alkaryl radicals having from about six to about 40 carbon atoms, halogen radicals, hydroxyl, alkoxy and aryloxy groups, and hydrocarbyl groups carrying halogen, hydroxyl, alkoxy or aryloxy, provided that at least one of each of $R_1$ to $R_8$ radicals is a sulfonato group or an alkyl, aryl, alkenyl, cycloalkyl, aralkyl or alkaryl carrying a sulfonato group, M is sulfur or oxygen, E is phosphorus, arsenic, antimony or nitrogen and F is phosphorus, arsenic or antimony.

2. A nickel ylide as defined in claim 1 wherein the sulfonato group is in $R_4$, $R_5$ and/or $R_6$ and at least one of $R_4$, $R_5$ and $R_6$ is aryl.

3. A nickel ylide as defined in claim 1 wherein the sulfonato group is in $R_1$, $R_2$ and/or $R_3$.

4. A nickel ylide as defined in claim 1 wherein $R_7$ comprises a sulfonato group.

5. A nickel ylide as defined in claim 1 wherein E and F are both phosphorus and M is oxygen.

6. A nickel ylide as defined in claim 2 wherein E and F are both phosphorus and M is oxygen.

7. A nickel ylide as defined in claim 3 wherein E and F are both phosphorus and M is oxygen.

8. A nickel ylide as defined in claim 4 wherein E and F are both phosphorus and M is oxygen.

9. A nickel ylide as defined in claim 6 wherein each of $R_4$, $R_5$ and $R_6$ is phenyl, one of which is substituted with a sulfonato group.

10. A nickel ylide as defined in claim 9 wherein each of $R_1$, $R_2$, $R_3$ and $R_8$ is phenyl and $R_7$ is hydrogen.

11. A nickel ylide as defined in claim 7 wherein each of $R_1$, $R_2$ and $R_3$ is phenyl, one of which is substituted with a sulfonato group.

12. A nickel ylide as defined in claim 11 wherein each of $R_4$, $R_5$, $R_6$ and $R_8$ is phenyl and $R_7$ is hydrogen.

13. A nickel ylide as defined in claim 8 wherein each of $R_1$, $R_2$, $R_3$, $R_4$, $R_5$, $R_6$ and $R_8$ is phenyl and $R_7$ is a sulfonato group.

14. The sodium salt of a nickel ylide as defined in claim 10.

15. The sodium salt of a nickel ylide as defined in claim 12.

16. The sodium salt of a nickel ylide as defined in claim 13.

17. The potassium salt of a nickel ylide as defined in claim 13.

18. The ammonium salt of a nickel ylide as defined in claim 13.

19. The trimethylammonium salt of a nickel ylide as defined in claim 13.

* * * * *

UNITED STATES PATENT AND TRADEMARK OFFICE
CERTIFICATE OF CORRECTION

PATENT NO. : 4,293,502
DATED : October 6, 1981
INVENTOR(S) : David L. Beach and James J. Harrison It is certified that error appears in the above-identified patent and that said Letters Patent are hereby corrected as shown below:

In the Abstract, 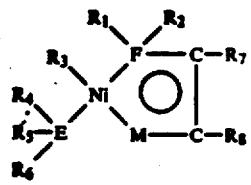 should read 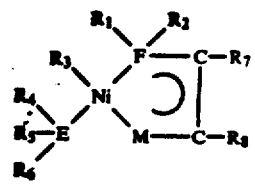

Column 8, line 17, "X" should read --x--.
Column 15, line 7, "nyldichlorophosophine" should read --nyldichlorophosphine--.

Signed and Sealed this

Fifth Day of October 1982

[SEAL]

Attest:

GERALD J. MOSSINGHOFF

Attesting Officer   Commissioner of Patents and Trademarks